United States Patent [19]
Sawin et al.

[11] Patent Number: 5,958,386
[45] Date of Patent: Sep. 28, 1999

[54] ANTIPERSPIRANT COMPOSITIONS CONTAINING SELECT COUPLING AGENTS

[75] Inventors: Philip Andrew Sawin, Cincinnati; Pamela Ann Keune, West Chester, both of Ohio

[73] Assignee: The Procter & Gamble Company, Cincinnati, Ohio

[21] Appl. No.: 09/096,258

[22] Filed: Jun. 11, 1998

[51] Int. Cl.⁶ .............. A61K 7/32; A61K 7/34; A61K 7/36; A61K 7/38; A61K 7/00
[52] U.S. Cl. .................. 424/65; 424/66; 424/67; 424/68; 424/400; 424/401
[58] Field of Search ................... 424/65, 66, 67, 424/68, 400, 401

[56] References Cited

U.S. PATENT DOCUMENTS

| | | | |
|---|---|---|---|
| 5,540,853 | 7/1996 | Trinh et al. | 424/401 |
| 5,833,999 | 11/1998 | Trinh et al. | 424/401 |
| 5,849,310 | 12/1998 | Trinh et al. | 424/401 |

*Primary Examiner*—Shelley A. Dodson
*Attorney, Agent, or Firm*—Joan B. Tucker; William J. Winter; Tara M. Rosnell

[57] ABSTRACT

Disclosed are antiperspirant compositions which comprise (a) from about 3% to about 40% by weight of a coupling agent comprising a combination of hexylene glycol and a hydrocarbon oil wherein the weight ratio of hexylene glycol to hydrocarbon oil is from about 1:2 to about 1:20; from about 0.5% to about 60% by weight of an antiperspirant active; from about 1% to about 15% by weight of a gellant selected from the group consisting of fatty acids, fatty acid esters, fatty acid amides, n-acyl amino acid derivatives, and mixtures thereof; and from about 10% to about 80% by weight of a volatile liquid carrier. The use of a combination of hexylene glycol and a hydrocarbon oil provides for improved coupling benefits at lower coupler concentrations, and allows for the formulation of an antiperspirant composition with good antiperspirant and aesthetic performance.

19 Claims, No Drawings

ANTIPERSPIRANT COMPOSITIONS CONTAINING SELECT COUPLING AGENTS

TECHNICAL FIELD

The present invention relates to antiperspirant compositions which contain a select coupling agent. In particular, the present invention relates to antiperspirant compositions which contain a coupling agent comprising a combination of hexylene glycol and a hydrocarbon oil.

BACKGROUND OF THE INVENTION

There are many types of topical antiperspirant products that are commercially available or otherwise known in the antiperspirant art. Most of these products are formulated as roll-on liquids, creams, emulsions, gels, gel-solids, or other solid stick formulations, and comprise an antiperspirant active and gellant incorporated into a suitable liquid carrier. These products are designed to provide effective perspiration and odor control while also being cosmetically acceptable during and after application onto the axillary area or other areas of the skin.

Many of these antiperspirant products comprising a gellant and liquid carrier are formulated at high processing temperature to solubilize the gellant in the liquid carrier. Typically, the gellant and other components except the antiperspirant active are added to a suitable liquid carrier and the solution is heated to a selected processing temperature to dissolve the gellant. Depending on the melting point of the selected gellant, the processing temperature can be increased or longer processing times used, but this can result in increased processing costs and lower gellant stability. Because it can be difficult to form a liquid solution of gellant and liquid carrier at the selected processing temperature, processing aids such as coupling agents are typically included in the formulation. It is well known that cosmetic emollients, e.g,. aliphatic fatty alcohols, are generally used as coupling agents in antiperspirant compositions to improve solubilization of the selected gellants and provide for a liquid solution of gellant and liquid carrier at the selected processing temperature, especially when the liquid carrier included in the composition contains a non-polar volatile silicone material.

Aliphatic fatty alcohols such as octyldodecanols are common cosmetic emollients that are particularly useful as coupling agents in anhydrous antiperspirant compositions because these solvents are readily soluble in non-polar volatile silicones and help to solubilize the gellant included in the composition. These particular coupling agents can also provide for the use of an increased amount of the volatile silicone oil, and the use of volatile silicone oils in antiperspirant compositions can provide highly desirable aesthetics benefits such as dry feel when the composition is applied to the skin. It has been found, however, that the use of some aliphatic fatty alcohols including octyldodecanol can interfere with antiperspirant efficacy and/or tend to feel greasy and sticky on the skin even when the aliphatic fatty alcohol is used in combination with a dry feeling solvent such as a volatile silicone.

It has now been found that a combination of a polar aliphatic alcohol, specifically hexylene glycol, and a hydrocarbon oil can be included in anhydrous antiperspirant compositions to improve coupling of the selected gellant with a volatile silicone liquid carrier. This select coupling agent combination is effective even at lower coupler concentrations, and helps to minimize the use of high concentrations of other emollient couplers which can interfere with antiperspirant efficacy and/or produce undesirable cosmetic aesthetics.

It has been surprisingly found that a solution of hexylene glycol, hydrocarbon oil, and a volatile silicone liquid carrier can result in a homogenous liquid mixture. This is surprising given that hexylene glycol is not miscible when used alone in combination with a hydrocarbon oil or a volatile silicone liquid carrier. It has been discovered, however, that the use of a select combination of hexylene glycol and a hydrocarbon oil at a certain weight ratio can provide not only homogenous liquid solutions of volatile silicone liquid carrier, hexylene glycol and a hydrocarbon oil, but can also provide improved coupling of the liquid carrier with the selected gellant.

It is therefore an object of the present invention to provide an antiperspirant composition which has good antiperspirant and aesthetic performance, and which contains a coupling agent comprising a select combination of hexylene glycol and a hydrocarbon oil. It is a further object of the present invention to provide an antiperspirant composition which contains a coupling agent that provides for improved coupling benefits.

SUMMARY OF THE INVENTION

The present invention is directed to antiperspirant compositions which comprise (a) from about 3% to about 40% by weight of a coupling agent comprising a combination of hexylene glycol and a hydrocarbon oil wherein the weight ratio of hexylene glycol to hydrocarbon oil is from about 1:2 to about 1:20; from about 0.5% to about 60% by weight of an antiperspirant active; from about 1% to about 15% by weight of a gellant selected from the group consisting of fatty acids, fatty acid esters, fatty acid amides, n-acyl amino acid derivatives, and mixtures thereof; and from about 10% to about 80% by weight of a volatile liquid carrier.

It has been found that antiperspirant compositions can be formulated to include a coupling agent comprising a combination of hexylene glycol and hydrocarbon oil to provide for improved coupling benefits. This select combination of coupling materials also provides for a homogenous liquid gellant matrix at selected processing temperatures.

DETAILED DESCRIPTION OF THE INVENTION

The antiperspirant compositions of the present invention are preferably anhydrous systems which comprise a gellant matrix within which a liquid carrier, coupling agent, and antiperspirant active are contained or held.

The term "anhydrous" as used herein means that the antiperspirant composition of the present invention, and the essential or optional components thereof other than the antiperspirant active, are preferably substantially free of added or free water. From a formulation standpoint, this means that the antiperspirant compositions of the present invention preferably contain less than about 5%, preferably less than about 3%, more preferably less than about 1%, most preferably zero percent, by weight of free or added water, other than the water of hydration typically associated with the antiperspirant active prior to formulation.

The term "ambient conditions" as used herein refers to surrounding conditions at about one atmosphere of pressure, at about 50% relative humidity, and at about 25° C., unless otherwise specified.

The term "coupling agent" as used herein refers to any compound, composition, or otherwise, which functions to bring the selected gellant and the liquid carrier defined herein into a homogenous liquid gellant matrix at processing temperatures of from about 60° C. to about 110° C.

The term "homogenous" as used herein refers to a liquid solution containing a gellant, coupling agent, and liquid carrier defined herein that appears to have the same uniformity and consistency when viewed by the naked eye at a processing temperature of above about 60° C.

The term "volatile" as used herein refers to materials which have a vapor pressure under ambient conditions of at least about 0.2 mm of Hg. Conversely, the term "non-volatile" as used herein refers to materials which have no measurable vapor pressure or which have a vapor pressure of less than about 0.2 mm of Hg under ambient conditions.

The antiperspirant compositions of the present invention can comprise, consist of, or consist essentially of the essential elements and limitations of the invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Coupling Agent

The antiperspirant compositions of the present invention comprise a coupling agent comprising a combination of hexylene glycol and one or more hydrocarbon oils. The total concentration of the coupling agent in the composition ranges from about 3% to about 40%, preferably from about 5% to about 30%, more preferably from about 5% to about 15%, by weight of the composition.

The coupling agent contains a combination of hexylene glycol and hydrocarbon oils wherein the hexylene glycol is present at concentrations ranging from about 5% to about 30%, preferably from about 10% to about 25%, more preferably from about 10% to about 20% by weight of the coupling agent; and wherein the hydrocarbon oils are present individually or combined at a total hydrocarbon oil concentration ranging from about 70% to about 95%, preferably from about 75% to about 90%, more preferably from about 80% to about 90% by weight of the coupling agent.

Any known or otherwise effective hydrocarbon oil material can be used in the antiperspirant compositions of the present invention, provided that the hydrocarbon oils are used in combination with hexylene glycol at a weight ratio of hexylene glycol to hydrocarbon oils of from about 1:2 to about 1:20, preferably from about 1:3 to about 1:10, more preferably from about 1:4 to about 1:10. It is known that some polyol-containing solvents such as hexylene glycol are not readily miscible in hydrocarbon oils or volatile silicone liquid carriers, especially cyclomethicone. It has been found, however, that hexylene glycol is miscible and can form a homogenous liquid solution or liquid dispersion with a volatile silicone liquid carrier when hexylene glycol is incorporated into a liquid solution of the silicone carrier as a combined weight ratio mixture of hexylene glycol and hydrocarbon oil. It is believed that the hydrocarbon oil helps to bring the hexylene glycol and liquid carrier into a homogenous liquid solution or liquid dispersion. The combination of hexylene glycol and hydrocarbon oil provides improved coupling performance which readily allows for the formation of a homogenous liquid gellant matrix containing the liquid carrier, coupling agent, and a selected gellant at the selected processing temperature. It has been found that the coupling performance provided by this select coupling system is extremely effective even when the coupling agent is included in the composition at lower coupler concentrations.

Nonlimiting examples of suitable hydrocarbon oils for use in the antiperspirant compositions of the present invention include volatile or non-volatile, non-polar hydrocarbon oils which can be cyclic, branched or chain configurations. In this context, the term "nonpolar" refers to those hydrocarbon oils having a solubility parameter of less than 8.0 $(cal/cm^3)^{0.5}$, preferably from about 5.0 $(cal/cm^3)^{0.5}$ to less than 8.0 $(cal/cm^3)^{0.5}$, more preferably from 6.0 $(cal/cm^3)^{0.5}$ to about 7.60 $(cal/cm^3)^{0.5}$. Specific non-limiting examples of suitable hydrocarbon oils include isohexadecane, isododecane, mineral oil, light mineral oil, petrolatum, isoparaffins, petroleum distallates, hydrogenated polyisobutenes, various other hydrocarbon oils, and combinations thereof. Preferred hydrocarbon oils include light mineral oil, isoparaffins, petrolatum, and combinations thereof.

Nonlimiting examples of preferred isoparaffins include those branched chain hydrocarbons oils which have from about 4 to about 30 carbon atoms, preferably from about 4 to about 20 carbon atoms, more preferably from about 6 to about 20 carbon atoms. Specific nonlimiting examples of these non-polar volatile hydrocarbon oils include the isoparaffins available from Exxon Chemical Company, Baytown, Tex. U.S.A, as Isopar M (C13–C14 isoparaffin), Isopar C (C7–C8 Isoparaffin), Isopar E (C8–C9 Isoparaffin), Isopar G (C10–11 Isoparaffin), Isopar L (C11–C13 Isoparaffin) and Isopar H (C11–C12 Isoparaffin).

Other nonlimiting examples of suitable hydrocarbon oils include Permethyl 99A (isododecane), Permethyl 102A (isoeicosane), Permethyl 101A (isohexadecane), and combinations thereof. The Permethyl series are available from Preperse, Inc., South Plainfield, N.J., U.S.A. Other nonlimiting examples of suitable branched chain hydrocarbons include petroleum distallates such as those available from Phillips Chemical as Soltrol 130, Soltrol 170, and those available from Shell as Shell Sol 70, -71, and -2033, and combinations thereof.

Other nonlimiting examples of suitable hydrocarbon oils include dodecane, octane, decane and combinations thereof, and the Norpar series of paraffins available from Exxon Chemical Company as Norpar 12, -13, and -15. Yet another example includes C11–C15 alkanes/cycloalkanes available from Exxon as Exxsol D80.

In addition to the hexylene glycol/hydrocarbon oil coupling agent, the antiperspirant composition may further comprise one or more optional coupling agents that are suitable for topical application to human skin. Optional coupling agents for use in combination with the hexylene glycol/hydrocarbon oil coupling agent include any known or otherwise effective coupling agent, provided that the resulting combination of coupling materials are miscible in the liquid carrier defined herein and can form a homogenous liquid solution or liquid dispersion with the liquid carrier and the selected gellant at the selected processing temperature of the composition. Such other optional coupling agents include, but are not limited to, dimethiconol, octyldodecanol, hexyldecanol, octyldecanol, undecylpentadecanol, isopropyl myristate, diisopropyl adipate, ethanol, diethyl phthalate, C12–C15 alcohol benzoates, and combinations thereof.

Antiperspirant Active

The antiperspirant compositions of the present invention comprise antiperspirant active, preferably particulate antiperspirant active, which is suitable for application to human skin. Suitable actives for use in the composition are preferably those which remain substantially unsolubilized as dispersed or precipitated solids in the composition. The concentration of antiperspirant active in the composition should be sufficient to provide the desired perspiration wetness and odor control from the antiperspirant formulation selected.

The antiperspirant compositions of the present invention comprise antiperspirant active at concentrations of from about 0.5% to about 60%, preferably from about 5% to about 35%, by weight of the composition. These weight percentages are calculated on an anhydrous metal salt basis exclusive of water and any complexing agents such as glycine, glycine salts, or other complexing agents. The antiperspirant active as formulated in the composition are preferably in the form of dispersed solid particles having a preferred average particle size or diameter of less than about 100 µm, more preferably from about 5 µm to about 50 µm, even more preferably from about 5 µm to about 40 µm.

The antiperspirant active for use in the antiperspirant compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions herein include those which conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydoroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the antiperspirant compositions herein include those which conform to the formula:

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825.146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

The antiperspirant compositions of the present invention can also be formulated to comprise other dispersed solids or other materials in addition to or in place of the antiperspirant active. Such other dispersed solids or other materials include any material known or otherwise suitable for topical application to human skin. The antiperspirant compositions can also be formulated to contain no antiperspirant or other active material, particulate or otherwise.

Gellant

The antiperspirant compositions of the present invention comprise a gellant suitable for topical application to human skin. Suitable gellents are those which can form in the composition a gellant matrix within which a liquid carrier, coupling agent, or other liquid component of the composition are contained.

The concentration of the gellents in the antiperspirant compositions may vary with each selected antiperspirant formulation, especially with each selected liquid carrier of the formulation, but such concentrations will generally range from about 0.1% to about 25%, preferably from about 1% to about 15%, more preferably from about 3% to about 12%, by weight of the composition.

Suitable gellants for use in the antiperspirant compositions herein are solids under ambient conditions. These solid gellants preferably have a melting point of from 60° C. to about 140° C., preferably from about 60° C. to about 120° C., more preferably from about 70° C. to about 110° C.

The gellants for use in the antiperspirant compositions of the present invention are those which can be solubilized and form a solution or other homogenous liquid or liquid dispersion with the selected liquid carrier, coupling agent, and other optional materials at a processing temperature of from about 28° C. to about 110° C., preferably from about 60° C. to about 110° C., more preferably from about 80° C. to about 100° C. The coupling agent defined herein is used to provide for solubilization or dispersion of the gellant throughout the selected liquid carrier to thus form a solution or other homogenous liquid. The solution or other homogenous liquid, and other essential and optional ingredients, are preferably combined in accordance with the manufacturing method described herein or other conventional or otherwise known technique, and then placed in a suitable package as a flowable homogenous liquid, and then allowed to solidify and form the desired gellant matrix within the composition as the temperature returns to ambient temperature and drops to below the solidification point of the selected gellant.

Gellants suitable for use in the antiperspirant compositions of the present invention include fatty acid gellants, esters and amides of fatty acid gellants, cholesterolic materials, lanolinolic materials, and other amide gellents known for use as gelling agents or which are otherwise described in detail hereinafter. Other gellants can be used in the antiperspirant compositions of the present invention provided that such other gellents can be formulated to provide the requisite gellant matrix and product characteristics defined herein.

Nonlimiting examples of suitable fatty acid gellents include, but are not limited to, fatty acid and hydroxy or alpha hydroxy fatty acids, having from about 10 to about 40 carbon atoms, examples of which include 12-hydroxystearic acid, 12-hydroxylauric acid, 16-hydroxyhexadecanoic acid, behenic acid, eurcic acid, stearic acid, caprylic acid, lauric acid, isostearic acid, and combinations thereof.

Preferred fatty acid gellants suitable for use in the antiperspirant compositions of the present invention include 12-hydroxystearic acid, esters of 12-hydroxystearic acid, amides of 12-hydroxystearic acid and combinations thereof. These preferred gellents include those which correspond to the following formula:

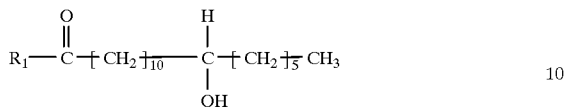

wherein $R_1$ is $OR_2$ or $NR_2R_3$; and $R_2$ and $R_3$ are hydrogen, or an alkyl, aryl, or arylalkyl radical which is branched linear or cyclic and has from about 1 to about 22 carbon atoms; preferably, from about 1 to about 18 carbon atoms. $R_2$ and $R_3$ may be either the same or different; however, at least one is preferably a hydrogen atom. Preferred among these gellants are those selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid, and combinations thereof. Most preferred is 12-hydroxystearic acid.

Suitable amide gellants for use in the antiperspirant compositions of the present invention include disubstituted or branched monoamide gellants, monosubstituted or branched diamide gellants, triamide gellants, and combinations thereof.

Non-limiting examples of suitable diamide and triamide gellants include select alkyl amides of a di- and/or tri-basic carboxylic acids which conform to the formula:

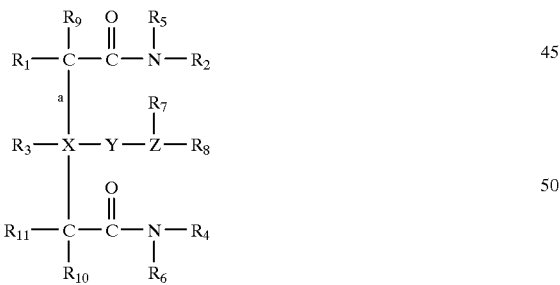

wherein a backbone is formed from the linkage of C', C" and X and wherein a) $R_1$ is nil, hydroxy, hydrogen, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{18}$ alkyl, $C_4$–$C_{18}$ alkenyl, $C_4$–$C_{18}$ alkoxy, $C_4$–$C_{18}$ alkyl esters, $C_4$–$C_{18}$ alkyl ethers, or $C_4$–$C_{18}$ alkyl substituted aryl, more preferably $C_{12}$–$C_{18}$ alkyl, $C_{12}$–$C_{18}$ alkenyl, $C_{12}$–$C_{18}$ alkoxy, $C_{12}$–$C_{18}$ alkyl esters, $C_{12}$–$C_{18}$ alkyl ethers, or $C_{12}$–$C_{18}$ alkyl substituted aryl;

b) $R_2$, $R_4$, $R_5$ and $R_6$ are independently or together, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

c) $R_3$ is nil, hydroxy, hydrogen, saturated or unsaturated, substituted or unsubstituted, straight, branched or cyclic chain $C_1$–$C_4$ alkyl, $C_1$–$C_4$ alkenyl, $C_1$–$C_4$ alkoxy, $C_1$–$C_4$ alkyl esters or $C_1$–$C_4$ alkyl ethers, preferably a $C_1$–$C_4$ alkoxy, hydroxy or hydrogen, more preferably a hydroxy or hydrogen;

d) $R_7$ and $R_8$ are independently or together, nil, hydrogen, hydroxy, aryl, siloxane or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl;

e) $R_9$ is nil or hydrogen;

f) and $R_{10}$ $R_{11}$ are independently or together, nil, hydrogen, hydroxy, aryl, siloxane or saturated or unsaturated, substituted or unsubstituted, straight, branched or cyclic chain $C_1$–$C_6$ alkyl, $C_1$–$C_6$ alkenyl, $C_1$–$C_6$ alkoxy, $C_1$–$C_6$ alkyl esters, $C_1$–$C_6$ alkyl ethers, or $C_1$–$C_6$ alkyl substituted aryl, preferably $C_1$–$C_4$ alkyl, $C_1$–$C_4$ alkenyl, $C_1$–$C_4$ alkoxy, $C_1$–$C_4$ alkyl esters, $C_1$–$C_4$ alkyl ethers, $C_1$–$C_4$ alkyl substituted aryl or hydrogen, more preferably a hydrogen;

g) X is nitrogen, aryl or $-(CH_2)_n-$ where n is an integer from 1 to 6, preferably $-(CH_2)_n-$ where n is an integer from 1 to 3;

h) Y is nil, acyl or carbonyl;

i) Z is nil, hydrogen, hydroxy, aryl, siloxane, nitrogen or saturated or unsaturated, substituted or unsubstituted, straight, branched or cyclic chain $C_1$–$C_{22}$ alkyl, $C_1$–$C_{22}$ alkenyl, $C_1$–$C_{22}$ alkoxy, $C_1$–$C_{22}$ alkyl esters, $C_1$–$C_{22}$ alkyl ethers, or $C_1$–$C_{22}$ alkyl substituted aryl, preferably $C_4$–$C_{10}$ alkyl, $C_4$–$C_{10}$ alkenyl, $C_4$–$C_{10}$ alkoxy, $C_4$–$C_{10}$ alkyl esters, $C_4$–$C_{10}$ alkyl ethers, or $C_4$–$C_{10}$ alkyl substituted aryl, more preferably $C_4$–$C_8$ alkyl, $C_4$–$C_8$ alkenyl, $C_4$–$C_8$ alkoxy, $C_4$–$C_8$ alkyl esters, $C_4$–$C_8$ alkyl ethers, or $C_4$–$C_8$ alkyl substituted aryl, and j) "a" is a double or single bond provided:
(i) when X and Z are not nil and Y is nil, X is directly bonded to Z;
(ii) when Z is nil, a hydrogen or a hydroxy, $R_7$ and $R_8$ are nil; and
(iii) when "a" is a double bond, $R_3$ and $R_9$ are nil.

Some specific examples of alkyl amides of di- and tribasic carboxylic acids suitable for use as a gellant herein include, but are not limited to, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N',N"-tri(methyldecylamide)amine, 2 docecyl-N,N'-dibutylsuccinamide, and combinations thereof. Preferred are alkyl amides di-carboxylic acids, more preferably 2 docecyl-N,N'-dibutylsuccinamide.

Preferred amide gellants include the n-acyl amino acid derivatives described in U.S. Pat. No. 5,429,816, issued to Hofrichter et al. on Jul. 4, 1995, which disclosure is incorporated herein by reference. Specific examples of preferred n-acyl amino acid derivatives include, but are not limited to, N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, and N-stearoyl-glutamic acid distearyl amide. Most preferred are n-lauroyl-glutamic acid dibutyl amide, n-stearyl-glutamic acid dihexyl amide, and combinations thereof.

The select alkyl amide gellants are preferably synthesized by direct amidation of the corresponding di- or tri-basic organic acid with the appropriate alkyl amine under suitable reaction temperatures, followed by removal of excess amine from the resulting mixture containing the alkylated amide gellants.

The select alkyl amide gellants may also be synthesized by esterification of the corresponding di- or tri-basic organic acid with methanol using a boron trifluoride catalyst followed by removal of the excess methanol and catalyst. The resulting trimethyl ester is then amidated using the appropriate alkylamine followed by removal of excess amine.

One preferred embodiment of the antiperspirant compositions of the present invention comprises a gellant combination of a fatty acid primary gellant and a n-acyl amino acid amide secondary gellant, wherein the molar ratio of primary gellant to secondary gellant is from about 1:2 to about 20:1, preferably from about 1:1 to about 10:1, more preferably from about 2:1 to about 7:1, and even more preferably from about 3:1 to about 5:1. It has been found that antiperspirant compositions comprising this gellant combination is more effective in providing low residue and aesthetics benefits compared to similar compositions containing either of the two gellents alone. It has now been found that the coupling agent defined herein can be used to provide improved coupling, of this select gellant combination with a volatile silicone liquid carrier, especially when the liquid carrier is volatile cyclomethicone.

Liquid Carrier

The antiperspirant compositions of the present invention comprise a liquid carrier that is a liquid under ambient conditions, and that preferably has a low viscosity to provide for improved spreading on the skin.

Concentrations of the liquid carrier in the antiperspirant composition will vary with the type of liquid carrier selected, the type of gellant used in combination with the liquid carrier and coupling agent, and the solubility of the selected gellant in a mixture of liquid carrier and coupling agent, and so forth. Preferred concentrations of the liquid carrier ranges from about 10% to about 80%, preferably from about 30% to about 70%, more preferably from about 45% to about 70%, by weight of the composition.

The liquid carrier comprises one or more liquid carriers suitable for topical application to human skin. These liquid carriers may be volatile silicones or non-volatile silicones, provided that the liquid carrier forms a solution or other homogeneous liquid or liquid dispersion with the coupling agent and selected gellant at the selected gellant concentration at a temperature of from about 28° C. to about 110° C., preferably from about 60° C. to about 110° C., preferably from about 80° C. to about 100° C.

The liquid carrier has a solubility parameter of from about 3 to about 13 $(cal/cm^3)^{0.5}$, preferably from about 5 to about 11 $(cal/cm^3)^{0.5}$, more preferably from about 5 to about 9 $(cal/cm^3)^{0.5}$. Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47–69, October 1988; and C. D. Vaughan, "Using Solubility Parameters in Cosmetics Formulation", 36 J. Soc. Cosmetic Chemists 319–333, September/October, 1988, which descriptions are incorporated herein by reference.

The liquid carrier preferably comprises one or more volatile liquid carriers. In this context, the term "volatile" refers to liquid carriers having a measurable vapor pressure under ambient conditions of at least about 0.2 mm of Hg.

Preferred volatile liquid carriers are the volatile silicone carriers, which includes cyclic, linear or branched chain volatile silicones. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred volatile silicone materials are those having from about 3 to about 7, more preferably from about 4 to about 5, silicone atoms. Cyclic silicones are most preferred.

Suitable cyclic silicones for use in the antiperspirant composition herein include those volatile silicones which conform to the formula:

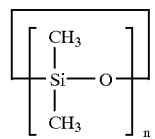

wherein n is from about 3 to about 7, preferably from about 4 to about 5, most preferably 5. These cyclic silicone materials will generally have viscosity values of less than about 10 cst at 25° C.

Suitable linear silicones suitable for use in the antiperspirant compositions herein include those volatile linear silicones which conform to the formula:

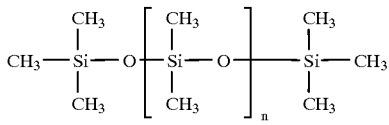

wherein n is from about 1 to about 7, preferably from about 2 to about 3. These linear silicone materials will generally have viscosity values of less than about 5 cst at 25° C.

Specific examples of volatile silicone carriers suitable for use in the antiperspirant compositions herein include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Other suitable carriers for use in the antiperspirant compositions of the present invention include non-volatile silicones. These non-volatile silicones will generally have viscosity values of up to about 100,000 centistokes, preferably less than about 500 centistokes, more preferably from about 1 centistoke to about 200 centistokes, even more preferably from about 1 centistoke to about 50 centistokes, as measured under ambient conditions. Examples of non-volatile silicones suitable for use in the antiperspirant compositions herein include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Electric Co.); and Silicone L-45, Silicone L530, Silicone L-531 (available from Union Carbide), and Siloxane F-221 and Silicone Fluid SWS-101 (available SWS Silicones).

Optional Components

The antiperspirant compositions of the present invention may further comprise one or more optional components which may modify the physical, chemical or aesthetic characteristics of the compositions or serve as additional "active" components when deposited on the skin. The compositions may also further comprise optional inert ingredients. Many such optional materials are known in the antiperspirant art and may be used in the antiperspirant compositions herein, provided that such optional materials are compatible with the essential materials described herein, or do not otherwise unduly impair product performance.

Nonlimiting examples of optional materials include active components such as bacteriostats and fungiostats, and "nonactive" components such as colorants, perfumes, emulsifiers, chelants, distributing agents, preservatives, residue masking agents, process aides such as viscosity modifiers, and wash-off aids. Examples of such optional materials are described in U.S. Pat. No. 4,049,792, Elsnau, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued Jul. 4, 1995; which descriptions are incorporated herein by reference.

The antiperspirant compositions of the present invention can also be formulated to comprise other dispersed solids or other materials in addition to or in place of the antiperspirant active. Such other dispersed solids or other materials include any material known or otherwise suitable for topical application to human skin. The antiperspirant compositions can also be formulated to contain no antiperspirant or other active material, particulate or otherwise.

Method of Manufacture

The antiperspirant compositions of the present invention may be prepared by any known or otherwise effective technique, suitable for providing an antiperspirant composition having the requisite homogeneous liquid gellant matrix and other product characteristics described herein. Such methods involve formulation of the essential components of the composition to form a homogenous liquid gellant matrix at processing temperatures below about 110° C.

Techniques for preparing the antiperspirant compositions of the present invention include those methods known in the antiperspirant art. A preferred method include combining the liquid carrier, selected gellant, and coupling agent. The combination is heated until it appears to be homogenous, which will typically occur for most combinations at a temperature of between about 60° C. and about 110° C. The resulting homogenous liquid is cooled or allowed to cool to between about 40° C. and about 100° C. at which time the solid antiperspirant active is added to and thoroughly mixed in the liquid along with any other optional ingredients. The resulting liquid mixture is then poured into containers and allowed to cool and solidify to the desired product hardness. Alternatively, the antiperspirant active or other optional ingredients can be added along with the liquid carrier, gellant and coupling agent, or at any other time that is suitable for such addition in order to manufacture the desired product form.

Method of Use

The antiperspirant compositions may be applied topically to the axilla or other area of the skin in an amount effective to treat or reduce perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied to the axilla or other area of the skin, one or two times daily, preferably once daily, to achieve effective antiperspirant and malodor control over an extended period.

EXAMPLES

The following nonlimiting examples illustrate specific embodiments of the antiperspirant compositions of the present invention, including methods of manufacture and use.

Each of the exemplified compositions are prepared by combining all of the listed components except the antiperspirant active and other materials such as perfumes. The combined components are heated to about 80° C. with agitation to form a hot liquid, after which all other materials are added to the heated liquid. The heated liquid is allowed to cool with agitation until just before the point of solidification, at which point the cooled, liquid composition is filled into applicator packages and allowed to cool and solidify to the requisite product hardness.

Each of the exemplified compositions comprise a gellant matrix containing gellant, antiperspirant active, coupling agent, and a liquid carrier. The coupling agent provides for improved coupling benefits at lower coupler concentrations, and allows for the preparation of the exemplified antiperspirant compositions which provide low residue performance, efficacy and aesthetics.

| Component | Example Number | | | | | |
|---|---|---|---|---|---|---|
| | I | II | III | IV | V | VI |
| Cyclomethicone D5 | 35.75 | 31.75 | 36.75 | 36.75 | 48.75 | 47.25 |
| Octyldodecanol | — | — | — | — | 6.00 | 6.00 |
| Mineral Oil | 26.00 | — | — | 13.00 | 8.00 | — |
| Petrolatum | — | 30.00 | — | — | — | 11.00 |
| Polydecene | — | — | 26.00 | — | — | — |
| Hydrogenated Polyisobutene | — | — | — | 13.00 | — | — |
| Hexylene Glycol | 3.25 | 3.25 | 3.25 | 3.25 | 2.00 | 1.00 |
| 12-Hydroxystearic Acid | 7.00 | 7.00 | 7.00 | 7.00 | 7.00 | 7.00 |
| N-lauroyl-glutamic acid dibutyl amide | 2.00 | 2.00 | 2.00 | 2.00 | 2.00 | 2.00 |
| Unilin 425 | — | — | — | 0.50 | 0.50 | — |
| Unilin 700 | 0.50 | 0.50 | 0.50 | — | — | — |
| Neodol 25-12 | — | — | — | — | 1.00 | 1.00 |
| Neodol 23-1 | — | — | — | — | 0.25 | 0.25 |
| Al Zr tri chlorohydrex glycinate | 24.00 | 24.00 | 24.00 | 24.00 | 24.00 | 24.00 |
| Disodium EDTA | 0.50 | 0.50 | 0.50 | 0.50 | 0.50 | 0.50 |
| Perfume | 1.00 | 1.00 | — | — | — | — |

What is claimed is:

1. An antiperspirant composition comprising:
   (a) from about 3% to about 40% by weight of a coupling agent comprising a combination of hexylene glycol and a hydrocarbon oil wherein the weight ratio of hexylene glycol to hydrocarbon oil is from about 1:2 to about 1:20;
   (b) from about 0.5% to about 60% by weight of an antiperspirant active;
   (c) from about 1% to about 15% by weight of a gellant selected from the group consisting of fatty acids, fatty acid esters, fatty acid amides, n-acyl amino acid derivatives, and mixtures thereof; and
   (d) from about 10% to about 80% by weight of a volatile liquid carrier.

2. The composition of claim 1 wherein the weight ratio of hexylene glycol to hydrocarbon oil is from about 1:3 to about 1:10.

3. The composition of claim 2 wherein the hydrocarbon oil is selected from the group consisting of isohexadecane, isododecane, isoeicosane, dodecane, octane, decane, mineral oil, light mineral oil, petrolatum, paraffins, isoparaffins, petroleum distallates, hydrogenated polyisobutenes, C11–C15 alkanes, C11–C15 cycloalkanes, and combinations thereof.

4. The composition of claim 2 wherein the gellant comprises fatty acids selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

5. The composition of claim 4 wherein the fatty acid is 12-hydroxystearic acid.

6. The composition of claim 2 wherein the gellant comprises n-acyl amino acid derivatives selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, and N-stearoyl-glutamic acid distearyl amide, and mixtures thereof.

7. The composition of claim 6 wherein the n-acyl amino acid derivative is N-lauroyl-glutamic acid dibutyl amide.

8. The composition of claim 2 wherein the composition comprises a combination of the fatty acid and n-acyl amino acid derivative at a molar ratio of fatty acid to n-acyl amino acid derivative of from about 1:2 to about 20:1.

9. The composition of claim 2 wherein the volatile liquid carrier is a cyclic silicone represented by the formula

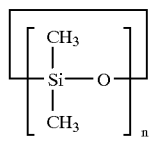

wherein n is from about 3 to about 7.

10. An antiperspirant composition comprising:
    (a) from about 3% to about 40% by weight of a coupling agent comprising a combination of hexylene glycol and a hydrocarbon oil wherein the weight ratio of hexylene glycol to hydrocarbon oil is from about 1:2 to about 1:20;
    (b) from about 0.5% to about 60% by weight of an antiperspirant active;
    (c) from about 1% to about 15% by weight of a combination of a fatty acid gellant and an amide gellant; and
    (d) from about 10% to about 80% by weight of a volatile cyclomethicone
wherein the composition has a molar ratio of fatty acid gellant to amide gellant of from about 1:2 to about 20:1.

11. The composition of claim 10 wherein the weight ratio of hexylene glycol to hydrocarbon oil is from about 1:3 to about 1:10.

12. The composition of claim 11 wherein the hydrocarbon oil is selected from the group consisting of isohexadecane, isododecane, isoeicosane, dodecane, octane, decane, mineral oil, light mineral oil, petrolatum, paraffins, isoparaffins, petroleum distallates, hydrogenated polyisobutenes, C11–C15 alkanes, C11–C15 cycloalkanes, and combinations thereof.

13. The composition of claim 11 wherein the fatty acid gellant is selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof.

14. The composition of claim 13 wherein the fatty acid gellant is 12-hydroxystearic acid.

15. The composition of claim 11 wherein the amide gellant is selected from the group consisting of n-acyl amino acid derivatives, alkyl amides of carboxylic acids, and mixtures thereof.

16. The composition of claim 15 wherein the n-acyl amino acid derivative is selected from the group consisting of N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, and N-stearoyl-glutamic acid distearyl amide, and mixtures thereof.

17. The composition of claim 16 wherein the n-acyl amino acid derivative is N-lauroyl-glutamic acid dibutyl amide.

18. A method for treating or reducing perspiration wetness and malodor, comprising applying from about 0.1 gram to about 20 grams of the composition of claim 1 to the desired area of the skin.

19. A method for treating or reducing perspiration wetness and malodor, comprising applying from about 0.1 gram to about 20 grams of the composition of claim 10 to the desired area of the skin.

* * * * *